US006416761B1

(12) United States Patent
Hjelle et al.

(10) Patent No.: US 6,416,761 B1
(45) Date of Patent: Jul. 9, 2002

(54) RIO MAMOR+e,ACU E+ee HANTAVIRUS NUCLEOCAPSID PROTEIN AND DIAGNOSTIC METHODS EMPLOYING SAID PROTEIN

(75) Inventors: Brian L. Hjelle; Norah Torrez-Martinez, both of Albuquerque, NM (US)

(73) Assignee: Science & Technology Corporation @UNM, Albuquerque, NM (US)

( * ) Notice: Subject to any disclaimer, the term of this patent is extended or adjusted under 35 U.S.C. 154(b) by 0 days.

(21) Appl. No.: 09/328,571

(22) Filed: Jun. 8, 1999

Related U.S. Application Data

(63) Continuation of application No. 08/673,230, filed on Jun. 27, 1996.
(51) Int. Cl.[7] .............................................. A61K 39/12
(52) U.S. Cl. ............................... 424/186.1; 424/204.1; 435/5; 435/7.1; 435/69.1
(58) Field of Search ..................... 435/5, 7.1; 424/218.1

(56) References Cited

U.S. PATENT DOCUMENTS 5,837,441 A * 11/1998 Hjelle et al. ................... 435/5

OTHER PUBLICATIONS

LeDuc, James W., et al., "Isolation of a Hantaan–Related Virus from Brazilian rats and Serologic Evidence of Its Widespread Distribution in South America," Am. J. of Tropical Med and Hygiene, vol. 34, No. 4, (Jul. 1985).

Lopez, Nora, et al., "Genetic Identification of a New Hantavirus Causing Severe Pulmonary Syndrome in Argentina," Virology vol. 220. pp 223–226 (Mar. 1996).

Jenison, S., et al., 1994, "Characterization of human antibody responses to four corners hantavirus infections among patients with hantavirus pulmonary syndrome", J. Virol. 68(5):3000–6.*

* cited by examiner

Primary Examiner—Laurie Scheiner
Assistant Examiner—Jeffrey S. Parkin
(74) Attorney, Agent, or Firm—Morgan, Lewis & Bockius, L.L.P.

(57) ABSTRACT

The Hantavirinae encompass a large number of species which are distributed worldwide. Although hantaviruses generally reside in murine hosts, they are also the causative agents of a number of human diseases including hantavirus pulmonary syndrome (HPS) and hemorrhagic fever with renal syndrome (HFRS). Tissue samples were obtained from hantavirus-infected rodents (e.g., *Oligoryzomys microtis*) and subjected to reverse transcription-polymerase chain reaction (RT-PCR) analysis to amplify hantaviral-specific nucleic acids. A molecular clone encoding the complete nucleocapsid (N) protein of the Rio Mamore Virus (RMV) was obtained and used to express high-levels of protein. The availability of the RMV N protein and its incorporation into immunodiagnostic assays will facilitate the detection of hantavirus-specific antibodies.

4 Claims, 7 Drawing Sheets

```
         v         v         v         v         v
            tagtagtagactccttgagaagctactACTGCATATGCTGGT          42 v         v         v         v         v
ATGAGCAACCTCCAAGAAGTACAAGAAGGTATCACACTCCATGAACAGCA              92
 M  S  N  L  Q  E  V  Q  E  G  I  T  L  H  E  Q  Q             17 v         v         v         v         v
GCTTGTAGCTGCTCGTCAAAAACTTAAGGATGCCGAGAAGGCAGTGGAAG             142
  L  V  A  A  R  Q  K  L  K  D  A  E  K  A  V  E  V            34 v         v         v         v         v
TGGACCCAGATGACGTTAACAAGAGCACATTACAAAGCAGACGGGCAGCT             192
   D  P  D  D  V  N  K  S  T  L  Q  S  R  R  A  A              50 v         v         v         v         v
GTGTCTACATTGGAGAATAAACTCGCAGAACTCAAGAGACAGCTGGCAGA             242
 V  S  T  L  E  N  K  L  A  E  L  K  R  Q  L  A  D             67 v         v         v         v         v
TTTGGTGGCAGCTCAAAAACTGGCTTCAAAACCAGTTGATCCAACAGGGC             292
  L  V  A  A  Q  K  L  A  S  K  P  V  D  P  T  G  L            84 v         v         v         v         v
TTGAGCCTGATGACCATTTAAAGGAGAAATCAGCTCTGCGATATGGGAAT             342
   E  P  D  D  H  L  K  E  K  S  A  L  R  Y  G  N              100 v         v         v         v         v
GTTCTGGATGTGAACTCTATAGATCTTGAAGAGCCTAGTGGTCAGACTGC             392
 V  L  D  V  N  S  I  D  L  E  E  P  S  G  Q  T  A             117
```

FIG.2A

```
           v         v         v         v         v
AGATTGGAAAGCAATCGGGGCATATATTTTAGGATTTGTCATACCGATTG        442
  D  W  K  A  I  G  A  Y  I  L  G  F  V  I  P  I  V      134 v         v         v         v         v
TCCTGAAAGCCTTATACATGCTTTCAACAAGGGGGAGGCAAACTGTCAAA        492
   L  K  A  L  Y  M  L  S  T  R  G  R  Q  T  V  K        150 v         v         v         v         v
GAGAACAAAGGGACAAGAATAAGGTTCAAGGATGACTCATCTTTTGAGGA        542
  E  N  K  G  T  R  I  R  F  K  D  D  S  S  F  E  E     167 v         v         v         v         v
AATAAATGGGATTAGGAAACCGAAACATCTGTATGTCTCCATGCCAACAG        592
  I  N  G  I  R  K  P  K  H  L  Y  V  S  M  P  T  A     184 v         v         v         v         v
CTCAGTCTACCATGAAGGCAGATGAGATCACACCAGGGAGGTTTCGAACA        642
   Q  S  T  M  K  A  D  E  I  T  P  G  R  F  R  T       200 v         v         v         v         v
ATTGCCTGTGGTTTATTTCCTGCACAAATCAAAGCTCGGAATATCATCAG        692
  I  A  C  G  L  F  P  A  Q  I  K  A  R  N  I  I  S     217 v         v         v         v         v
TCCAGTGATGGGGGTGATTGGGTTTGGGTTCTTTGTAAAGGACTGGATGG        742
   P  V  M  G  V  I  G  F  G  F  F  V  K  D  W  M  D    234 v         v         v         v         v
ATAGGATAGAAAGTTTTTTAGCAGCTGAATGCCCATTCCTCCCAAAACCA        792
   R  I  E  S  F  L  A  A  E  C  P  F  L  P  K  P       250
```

FIG.2B

```
              v         v         v         v         v
AAGGCCCAATCAGAATCTTTCATGGGGACTAACAGGGCTTATTTTATCAA          842
 K  A  Q  S  E  S  F  M  G  T  N  R  A  Y  F  I  N         267 v         v         v         v         v
CCGTCAGAGGCAAGTGGATGAATCAAAGATTCCTGAAATAGTTGACCTCA          892
 R  Q  R  Q  V  D  E  S  K  I  P  E  I  V  D  L  I         284 v         v         v         v         v
TTCAAGCAGCAGAGTCAAAGTCAGCCACATTATTCAATGATATTGCAGTC          942
  Q  A  A  E  S  K  S  A  T  L  F  N  D  I  A  V          300 v         v         v         v         v
CCTCATTCTGTGTGGGTTTTTTCATGTGCTCCTGATAGATGCCCCCCAAC          992
 P  H  S  V  W  V  F  S  C  A  P  D  R  C  P  P  T         317 v         v         v         v         v
TGCACTTTATGTTGCAGGAGTTCCTGAGCTTGGGGCATTTTTCTCAATCC         1042
  A  L  Y  V  A  G  V  P  E  L  G  A  F  F  S  I  L       334 v         v         v         v         v
TGCAGGACATGCGAAATACAATCATGGCATCAAAGTCTGTCGGAACAGCA         1092
  Q  D  M  R  N  T  I  M  A  S  K  S  V  G  T  A          350 v         v         v         v         v
GAAGAGAAGTTGAAGAAGAAATCAGCTTTCTACCAATCATATTTAAGAAG         1142
 E  E  K  L  K  K  K  S  A  F  Y  Q  S  Y  L  R  R        367 v         v         v         v         v
GACTCAGTCAATGGGAATTCAACTGGACCAGAAGATCATCATATTATACA         1192
 T  Q  S  M  G  I  Q  L  D  Q  K  I  I  I  L  Y  M        384
```

FIG.2C

```
                  v         v         v         v         v
         TGCTCTTTTGGGGTAAAGAAGCTGTAAACCACTTTCATCTCGGGGATGAC          1242
            L  F  W  G  K  E  A  V  N  H  F  H  L  G  D  D          400 v         v         v         v         v
         ATGGATCCTGAACTCAGGCAGCTAGCACAATCTCTGATTGATGCAAAGGT          1292
            M  D  P  E  L  R  Q  L  A  Q  S  L  I  D  A  K  V       417 v         v         v         v         v
         GAAAGAAATTTCAAACCAAGAGCCATTGAAATTGTAAGAGGAAAGAAGGC          1342
            K  E  I  S  N  Q  E  P  L  K  L  <             428 v         v         v         v         v
         AAAGATGGGTTTCCGGGCTTGTGCCAACAGTTATTCATCTCTGGACTATT          1392 v         v         v         v         v
         CTGCACTAATCAATGTGATAGAGTTAAGGTAGTTAGAATGTGAAGGGTGG          1442 v         v         v         v         v
         TGGGGGGTGACATTACAAGGGTGGGATTGTTTACTCACATGGGTTCTAGG          1492 v         v         v         v         v
         GCCATATTACGTAATTGCACTATAAATTGTGATAGCCATAATAAGTAAAT          1542 v         v         v         v         v
         TACACTACATAATGAGATATAGATGTAGGTTAAGTTTACCTTATGATTTG          1592 v         v         v         v         v
         ATCAAATGATGCATTGCTGATTGATCAAGGACTAATGAATGTAATCAGGA          1642 v         v         v         v         v
         TGCATAGTTGTTTAAATCATAGATCCATATAGTGTTAAGTCATAGATTTA          1692
```

FIG.2D

```
                v         v         v         v         v
           AATCATAAGTTTAAGTTAGGCATTGGTTTAAGTTAAGTTTAGATTTAGAT        1742 v         v         v         v         v
           TTAGGTTAAGTATAGGTTTGATAGAGTAAATTCATAGATTTTGTTCCCTC        1792 v         v         v         v         v
           AAGTTAAATTTACTAAAAATTTAATGCCATTGGATGTAAATTTCATTCCT        1842 v         v         v         v         v
           GCTTAAGCTTTGCAATACTAACACTAACTCAACACATTCCTACCTCATCC        1892 v         v         v         v         v
           CAATACCCTTCCCTTTTATTCTACCTCATTTATTCTACCTTATCAGTTAT        1942 v         v         v
           TTTCTTGAttgcttttcaaggagtatactacta        1975
```

RIO MAMOR+e,ACU E+ee HANTAVIRUS NUCLEOCAPSID PROTEIN AND DIAGNOSTIC METHODS EMPLOYING SAID PROTEIN

This application is a continuation of Ser. No. 08/673,230 filed Jun. 27, 1996.

BACKGROUND OF THE INVENTION

1. Field of Art

Hantaviruses

Hantaviruses are a group of at least 19 diverse agents. They occur worldwide in rodent hosts and cause either (1) no known human disease; (2) hemorrhagic fever with renal syndrome, HFRS, or (3) Hantavirus pulmonary syndrome (HPS) when transmitted to man. The following is a compilation of currently recognized types; there is not universal agreement among workers in the field as to the degree to which each is clearly distinct from each other:

| Virus | High density particle agglutination | IFA* | ELISA** | Western blot |
|---|---|---|---|---|
| Hantaan | C | C | C | D |
| Seoul | C | C | C | D |
| Puumala | C | C | C | C/D |
| Sln Nombre | | D | C | C |
| Dobrava | | D | D | |

*IFA, immunofluorescence assay
**ELISA, enzyme-linked immunosorbent assay. Both native (cultured virus) and recombinant-expressed antigens are used.

| Virus | Abbreviation | Synonyms | Host | Distribution of Host | Disease |
|---|---|---|---|---|---|
| Hantaan | HTN | | A. agrarius | Central & E Asia, Central & E Europe | HFRS |
| Seoul | SEO | Baltimore rat virus; many others | R. norvegicus, R. rattus | Worldwide; commensal rat hosts | HFRS |
| Dobrava/Belgrade | DOB | BEL | A. flavicollis | Asia Minor Europe, Palestine | HFRS |
| Puumala | PUU | | C. glareolus | Russia, Europe, Asia Minor | HFRS |
| Sin Nombre | SN | Four Corners; Muerto Canyon; Convict Creek | P. maniculatus | Throughout US, W Canada | HPS |
| Black Creek Canal | BCC | | S. hispidus | SE US to Peru | HPS |
| Muleshoe | MULE | | S. hispidus | W. Texas | unknown |
| Monongahela | MON | | P. maniculatus | Appalachians, W. Va. to New York | unknown |
| New York | NY | SI-1 | P. leucopus | NE US, SE Canada | HPS |
| Bayou | BAY | | O. palustris | SE US, Kansas to New Jersey | HPS |
| Thottapalayam | TPM | | S. murinus | Africa, India, SE Asia | unknown |
| Tula | TUL | | M. arvalis | Russia, Europe, Asia Minor | unknown |
| Thai | THAI | | B. indica | SE Asia, India | unknown |
| Prospect Hill | PH | | M. pennsylvanicus | N, E US, Canada, Alaska | unknown |
| Bloodland Lake | BLLL | PVV | M. ochrogaster | Midwestern, E US, S Canada | unknown |
| Khabarovsk | KBR | | M. fortis | E Russia | unknown |
| Isla Vista | ILV | CMMV | M. californicus | California, Oregon, Mexico | unknown |
| El Moro Canyon | ELMC | HMV-1 | R. megalotis | W US, Mexico, SW Canada | unknown |
| Rio Segundo | RIOS | HMV-2 | R. mexicanus? | Mexico, Costa Rica, Ecuador | unknown |
| Rio Mamoré | RM | | Oligoryzomysmicrotis | Bollvia, Brazil, Paraguay, Peru, Argentina | unknown |

Since there are so many distinct species of Hantaviruses, there is no single test or single reagent that allows the diagnosis of all hantavirus infection. In each case, the best reagents for detection of antibodies to a given hantavirus are those which are based upon the hantavirus species that actually caused the infection. The nucleocapsid (N) protein is the portion of each hantavirus that is most strongly immunogenic, and the standard for diagnosis of Hantaviruses has increasingly been to rely upon the expression of homologous N protein in bacteria or other microbial expression system to generate high concentrations of recombinant-expressed antigen. Classical methods of viral antibody detection have depended upon the growth of the virus in culture, with use of the viral antigens from infected cultures in immunologic detection, but these methods are increasingly falling out of favor for a variety of technical and practical reasons.

2. Discussion of Related Art

Specific diagnostic tests are available for several previously-described Hantaviruses. For Hantaviruses in general, antibody tests are much preferred over direct detection of infectious viral particles, viral genomic RNA, or viral antigens because of the inherently superior stability, sensitivity, specificity, and ease of transfer of antibody assay technologies. The following modalities are in common use (C) or are under development or research use (D) for the following Hantaviruses:

Because none of the prototype Hantaviruses listed above occurs in rodents with distribution in South America, it is virtually certain that human Hantavirus disease in South America is due to novel virus(es) that will be detected in a less-than-optimal manner by tests that utilize antigens derived from prototype species. These virus(es) are almost certainly associated with indigenous rodents of the subfamily Sigmodontinae, family Muridae, because the clinical disease that has been noted in Brazilian, Argentinean, and Paraguayan patents is closely similar to those diseases caused by North American Hantaviruses of sigmodontine rodents. Detection of Hantavirus infection in South America has relied most heavily upon cross-reactivity between the prototypic sigmodontine rodent-borne Hantavirus Sin Nombre (Four Corners) virus (SNV) and the South American virus(es).

SUMMARY OF THE DISCLOSURE

The invention provides a molecular clone encoding and expressing the complete nucleotide protein of Rio Mamoré virus. The RMV N protein includes antigenically active domains useful in immunoassays for detecting South American Hantavirus infection, and in vaccines.

BRIEF DESCRIPTION OF THE DRAWINGS

FIG. 1. Consists of FIGS. 1A through 1E. FIG. 1E is a dried polyacrylamide gel containing 4 different protein preparations. The first lane ("C") is a crude lysate of *E. coli* JM101 cells after induction of expression from the pET23b vector that lacks a viral genetic insert. The next 3 lanes contain the pET23b-expressed, affinity-purified viral N proteins from Bayou (BAY), Rio Mamoré (RM) or Sin Nombre (SN)Hantaviruses. 4 western blot membranes containing the same purified proteins are at left. Panels (clockwise from upper left) were probed with serum of (FIG. 1A) an RMV-infected *Oligoryzomys microtus* mouse; (FIG. 1B) a BAYV-infected rice rat (*Oryzomys palustris*) from Texas; (FIG. 1C) an uninfected deer mouse (*Peromyscus maniculatus*); (FIG. 1D) an SNV-infected deer mouse (*Peromyscus maniculatus*) from Texas. Antibodies were detected with an alkaline phosphatase-conjugated goat anti *P. leucopus* reagent, followed by exposure to alkaline phosphatase substrate as described (Jenison et al., 1994). The dark bands in the BAY, RMV, and SNV lanes indicate the presence of antigenically-active N protein that reacts with rodent serum. All N proteins are about 55 kD in apparent molecular weight Differential reactivity is evident in each panel, in each case stronger reactivity is evident against the homologous viral antigen.

DETAILED DESCRIPTION OF THE INVENTION

Medically-important Hantaviruses generally are associated with ecologically dominant murid rodent species. Oryzomine rodents were selected as potentially important vectors of human Hantavirus disease in South America because (1) they are abundant, widespread, and occur in high density; (2) they favor disturbed habitat such as houses and other human habitations; (3) was recently identified as a North American oryzomine rodent, *Oryzomys palustris* is the host for an etiologic agent of HPS (Bayou virus) in Louisiana and Texas. Accordingly, tissue specimens of candidate oryzomine rodent hosts were obtained from the Museum of Southwestern Biology (University of New Mexico) and from the Museum of Vertebrate Zoology (University of California, Berkeley). These included:

| Date Captured | Jurisdiction | Country | Species | tested | positive |
| --- | --- | --- | --- | --- | --- |
| 1994 | Bollvar Province | Ecuador | *Microryzomys sp.* | 1 | 0 |
| 1994 | Bollvar Province | Ecuador | *Oryzomys albigularis* | 12 | 0 |
| 1991 | Amazonas State | Brazil | *Oryzomys capito* | 20 | 0 |
| 1991–1992 | Acre and Amazonas States | Brazil | *Oryzomys yunganus* | 29 | 0 |
| 1991 | Amazonas State | Brazil | *Oligoryzomys microtis* | 32 | 0 |
| 1991 | Acre and Amazonas State | Brazil | *Oecomys bicolor* | 6 | 0 |
| 1991 | Acre and Amazonas States | Brazil | *Oecomys roberti* | 13 | 0 |
| 1977–79 | Amazonas Dept. | Peru | *Oryzomys capito* | 14 | 0 |
| 1977–79 | Amazonas Dept. | Peru | *Nectomys squamlpes* | 2 | 0 |
| 1977–79 | Amazonas Dept. | Peru | *Oecomys bicolor* | 15 | 0 |
| 1985 | Beni Dept. | Bollvia | *Oligoryzomys microtis* | 10 | 3 |
| 1985, 1992 | La Paz Dept. | Bollvia | *Oligoryzomys microtis* | 12 | 2 |
| 1984–85 | Santa Cruz Dept | Bollvia | *Oligoryzomys microtis* | 13 | 0 |
| 1984, 1991 | Santa Cruz and Tarija Depts. | Bollvia | *Oligoryzomys flavescens* | 9 | 0 |
| 1990–91 | Santa Cruz, Chuquisaca, and Tarija | Etquitsia | *Oligoryzomys chacoensis* | 5 | 0 |
| | | | Total | 192 | 5 |

Briefly, the supernatants of these tissue (kidney, heart, and/or liver) samples were screened for Hantavirus antibodies using a recombinant western blot assay for antibodies reactive with SNV (see PCT/US94/09416). The antigen comprised the recombinant-expressed TrpE-SNV N fusion protein, which was transferred to a nitrocellulose membrane as described in PCT/US94109416 (Jenison S, Yamada T, Morris C, Anderson B, Torrez-Martinez N, Keller N, Hjelle B., "Characterization of human antibody responses to Four Corners Hantavirus infections among patients with hantavirus pulmonary syndrome." *J Virol* 1994; 68:3000–6). The membrane strips were rocked overnight at 4° in a bath containing 5% dry milk in phosphate-buffered saline and a 1:200 dilution of tissue sample supernatant (as source of antibodies). Bound antibodies were detected with a secondary antibody consisting of alkaline phosphatase-conjugated goat anti-*Peromyscus leucopus* IgG.

Of the above specimens, only 5 (all *Oligowyzomys microtis* from Bolivia, collected in 1985) were positive for Hantavirus antibodies. These tissue samples were used to prepare RNA, and the RNA was then subjected to reverse transcription-polymerase chain reaction (RT-PCR) analysis to identify the virus and to prepare recombinant antigens through expression of the PCR-amplified DNA in molecular clones.

The availability of a molecular clone encoding the complete N protein of Rio Mamoré Virus (RMV) makes it possible to detect Hantavirus infection in South American people and rodents with homologous antigens for the first time. The high-level expression of the N protein allows incorporation into a variety of antibody testing formats to produce the most efficient and accurate diagnostic tests. The RMV N protein is antigenically active in western blot and ELISA formats. Additional conventional formats such as immunofluorescence assay, particle agglutination and radio-immunoprecipitation assays are contemplated.

Serologic (antibody) tests to screen for, or confirm, the presence of antibodies to RMVN protein, whether in humans, rodents, or other animals are described herein. The western blot and ELISA assays have been reduced to practice, and other methods are readily adapted from these procedures (given the purified antigen) by trivial manipulations. Although many different configurations are within the scope of the invention, an ELISA system in which a microtiter well is first coated with goat IgG directed against human IgM is of particular interest. The well is then treated with the serum of a patient with suspected RMV infection, washed, then treated with purified recombinant antigen. After washing, a biotin-labeled rabbit antibody directed against the recombinant antigen of RMV (see below) is applied. Finally a streptavidin-conjugated alkaline phosphatase is used to detect the bound biotin. A chromogenic alkaline phosphatase substrate is used to detect bound alkaline phosphatase.

Even in the event that laboratory is able to grow RMV in culture, and develop an ELISA based upon the native antigens of the culture-adapted virus, rDNA-derived antigens will continue to be useful diagnostic tools. In many cases rDNA antigens provide valuable supplementary information to that provided by ELISAs using cultured virus as antigen; in some cases, rDNA antigens have superior sensitivity or superior ability to differentiate among antibodies directed against different related viruses, or ability to diagnose infection by viruses for which there is no method of culture. At present, virtually all North American HPS virus infections are diagnosed with recombinant antigen-based systems.

I. Experimental Methods

Design of PCR Primers.

Reaction Mixes and Conditions: Reverse Transcription and "First Round" PCR.

The initial reaction mixes (for reverse transcription and subsequent PCR thermal cycling) were as follows. All mixtures contained 10 pmol of each primer; 1.7 mM 2-mercaptoethanol; 1.5 mM $MgCl_2$; 10 mM Tris-HCl (pH 8.3); 50 mM KCl; 200 uM each of dATP, dTTP, dGTP, and dCTP; 10 units of AMV reverse transcriptase (Boehringer-Mannheim), and 2.5 units of AmpliTaq™ DNA polymerase (Perkin-Elmer), in a final volume of 100 ul. After addition of all reagents to a 0.6 ml Eppendorf tube, the tubes were overlaid with 3 drops of mineral oil (Perkin-Elmer), and placed in a thermal cycler. Each tube was warmed to 42° C. for 1 h, then subjected to temperature cycling of 94°–40°–72° for 1 minute, 1 minute, and 3 minutes per cycle for 8 cycles, then 94–45–72° (1 minute, 1 minute, and 3 minutes) for 29 more cycles.

"Second Round" PCR.

After the initial amplification described above, all of the samples were subjected to some form of "nesting" PCR reaction, in which the amplified product was further amplified by using primers internal to those used in the first round of amplification. Fifty pmol of each "second round" primer was used; reaction ingredients included 3 ul of the first-round PCR product, and the same ingredients as those in the first round (except no 2-mercaptoethanol or reverse transcriptase was added):

The "second round" PCR product was prepared by thermal cycling at 94–40–72 (1 minute, 1 minute, and 3 minutes, respectively) for 8 cycles, followed by 29 more cycles at 94–42–72 (1 minute, 1 minute, and 3 minutes, respectively). The reaction was then subjected to an elongation step of 70° for 10 minutes. The DNA product was then loaded on an 1.2%–1.6% agarose gel, electrophoresed for 1 h at 80V, and the band of the appropriate molecular weight was then excised with a razor blade. The DNA was extracted from the gel with a glass-milk resin (Qiaex resin, Qiagen Inc.) after melting the gel in a sodium iodide solution. After washing the resin (according to the instructions for Qiaex resin), the PCR product was taken up in 10 ul of (10 mM Tris-HCl, pH 8/1 mM EDTA), and 5–10 ul was ligated to the pCRII vector according to the manufacturer's instructions (Invitrogen Corp.). One ul of the 10 ul ligation mix was used to transform E. coli cells according to the manufacturer's instructions (Invitrogen), and the transformed cells plated onto LB media containing 50 ug/ml ampicillin and 0.005% X-Gal; plates were incubated at 37° overnight. Clear colonies were selected from the plate the following morning and expanded in 4 ml of LB media containing 50 ug/ml ampicillin.

All PCR primers were designed either as consensus primers (conserved portions of other Hantavirus S segments that were predicted to be conserved in RMV) or by directly reading the sequences of RMV clones and designing primers from those sequences.

Primers (S genomic segment) successfully used in amplifying RMV cDNAs:

| Primer number (primer type) | Coordinate (S segment) | Sequence (5'-3') | |
|---|---|---|---|
| 1 (C*) | 1 sense | TAG TAG TAG ACT CCT TGA GAA GCT AC | (SEQ ID NO:1) |
| 2 (RMV) | 25 sense | ACT ACT GCA TAT GCT GGT ATG AG | (SEQ ID NO:2) |
| 3 (RMV) | 1688 antisense | TCT ATG ACT TAA CAC TAT ATG GAT C | (SEQ ID NO:3) |
| 4 (RMV) | 43 sense | T AAG CTT ATG AGC MC CTC CAA GAA GTA CAA GA | (SEQ ID NO:4) |
| 5 (RMV) | 1326 antisense | C CTC GAG CAA TTT CAA TGG CTC TTG GTT TGA | (SEQ ID NO:5) |
| 6 (RMV) | 997 sense | CTT TAT GTT GCA GG(AT) GT(TA) CCT GA | (SEQ ID NO:6) |
| 7 (RMV) | 1039 sense | ATC CTG CAG GA(CT) ATG (CA)GA AAT AC | (SEQ ID NO:7) |
| 8 © | 184 sense | CGG GCA GCT GTG TCT GCA TTG GA | (SEQ ID NO:8) |

-continued

| Primer number (primer type) | Coordinate (S segment) | Sequence (5'-3') | |
|---|---|---|---|
| 9 © | 626 antisense | GG TGT GAT TTC ATC TGC (C/T) TT CAT | (SEQ ID NO:9) |
| 10 © | 1085 antisense | CC TAC AGA CTT TGA TGC CAT (GAT) AT | (SEQ ID NO:10) |
| 11 © | 1975 antisense | TAG TAG TAT ACT CCT TGA AAA GCA A | (SEQ ID NO:11) |

*(C)= consensus hantavirus primer; (RMV) = primer designed from empirically-determined sequences of RMV sample OM NK 13556. Bolded sequences in primers 4 and 5 represent restriction endonuclease sites that were introduced as the primers were designed. All coordinates refer the location of the 5'-most residue of the primer; each primer is written in 5'-3'direction.

The following primer combinations were used in cloning the RMV S genome, in the indicated order:

1. Primers 1 and 10, nested with primers 8 and 9, yielding a 442-nt product. Tissue RNAs from five seropositive *O. microtus* were used in this round, and all were positive. Since specimen OM NK 13556 (from Beni Department, Bolivia) produced the strongest amplification signal, it was used exclusively in further amplification reactions, and represents the prototype RMV S segment sequence.

2. Primers 1 and 10, heminested with primers 8 and 10, yielding a 901-nt product The sequence of this product was used to synthesize primers 6 and 7.

3. Primers 6 and 11, heminested with primers 7 and 11, yielding a 939-nt product, spanning the 3' end of the gene.

4. Primers 1 and 10, heminested with primers 1 and 9, yielding a 626-nt product that spanned the 5' end of the gene.

5. The intact N gene open reading frame was then cloned by amplifying with primers 2 and 3, followed by nesting with primers 4 and 5, yielding a 1287-nt product.

Plasmid DNA was prepared from the cultures according to standard methods, and then digested with various restriction enzymes to verify that the correct insert had been obtained. Clones that appeared to have the correct restriction enzyme digestion pattern were subjected to DNA sequencing (according to the manufacturer of the Sequenase™ sequencing system, US Biochemicals) to verify that DNA with characteristics appropriate for a novel Hantavirus had been amplified and cloned. The DNA was examined for strong homology to (but not identity to) previously-described Hantaviruses SNV and Bayou virus, and relative conservation of the protein product that would be predicted from the nucleotide sequence.

II. Expression of the RMV N Protein

The complete N gene open reading frame was excised from the cloning vector pCRII, and subcloned at the Hind III and Xho I restriction sites (which were incorporated into the PCR primers 2 and 3). The gene was transferred into the pET 23b vector (Novagen Inc.) at the Hind III and Xho I sites and expanded in *E. coli* strain BL21, wherein the gene is not expressed. This vector places the N gene in fusion with a small leader genetic element derived from the T7 bacteriophage. Correct clones were identified by restriction endonuclease digestion and DNA sequencing. The clone was then transfected into the expression-competent cell, BL21 (DE3), where N gene expression was induced with IPTG according to the manufacturers instructions.

Induction with IPTG resulted in the high-level production of a band at approximately 55,000 Daltons apparent molecularweight by SDS-polyacrylamide gel electrophoresis. A band of identical size was produced with a control induction that results in the expression of a T7-Bayou Hantavirus N protein, and a somewhat larger band was produced by expression of the Sin Nombre virus N protein as 2 Trp E fusion partner (the larger size of the SNV N protein is explained by the larger size of the Trp E fusion partner relative to the T7 fusion partner). The proteins on the SDS gel were transferred to a nitrocellulose membrane by western blotting (Jenison S, Yamada T, Morris C, Anderson B, Torrez-Martinez N, Keller N, Hjelle B. Characterization of human antibody responses to Four Corners Hantavirus infections among patients with Hantavirus pulmonary syndrome. *J Virol* 1994; 68:3000–6). To verify that the RMV N protein produced in this manner is antigenically active, the western blot was probed with serum from a patient with SNV-induced HPS, and all three N proteins (RMV, BAYV, and SNV) were strongly reactive. By contrast, a lane in which the pET 23b vector alone was used in induction experiments yielded no immunoreactive bands, and a serum from a patient without HPS also produced no. bands.

Figure 1A:
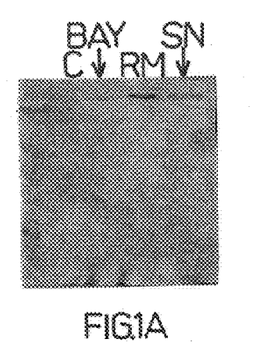
Figure 1B:
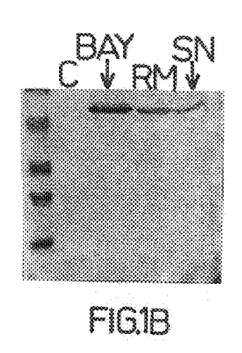
Figure 1C:
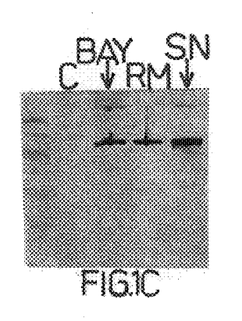
Figure 1D:
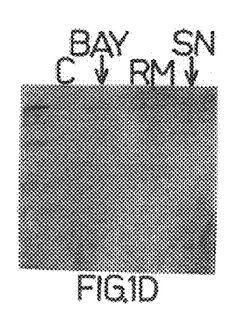
Figure 1E:
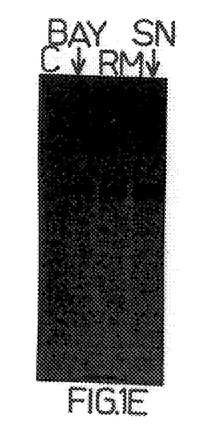
Figure 2A:
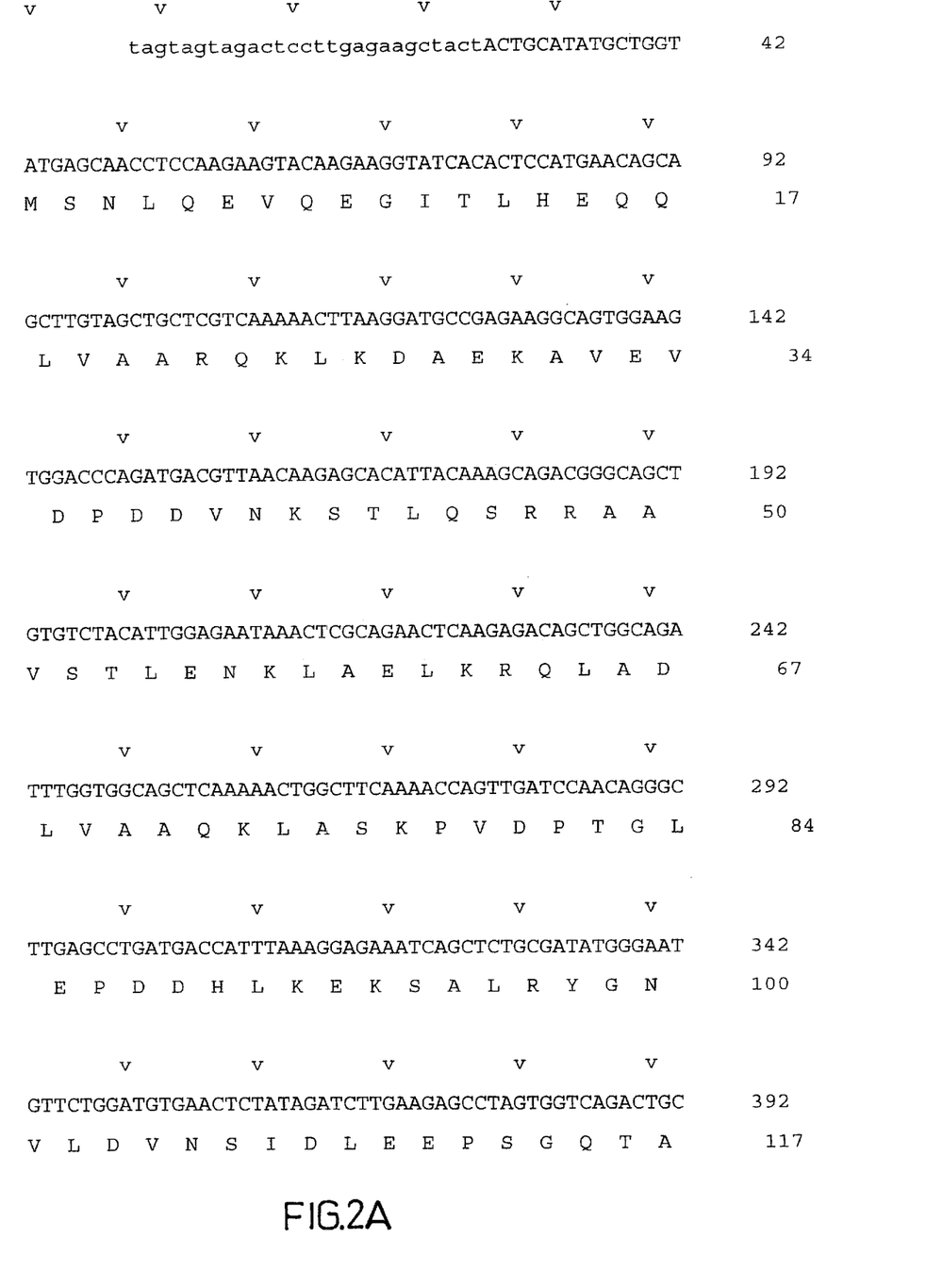
FIG. 2. Consists of FIGS. 2A through 2E. The complete sequence of the S genomic segment (SEQ ID NO: 12) and associated N protein (SEQ ID NO: 13) of Rio Mamoré virus, specimen OM NK 13556.
Figure 2B:
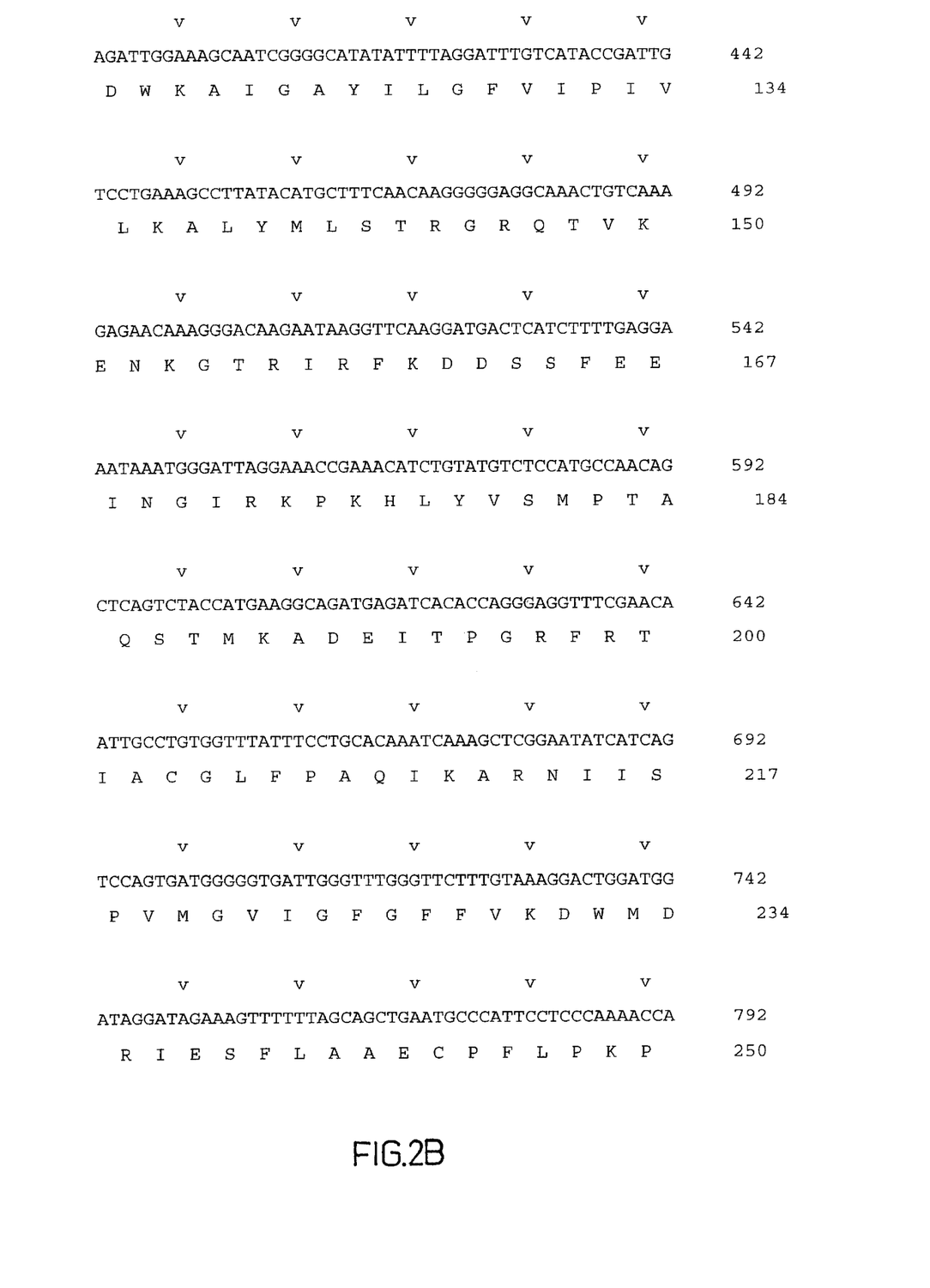
Figure 2C:
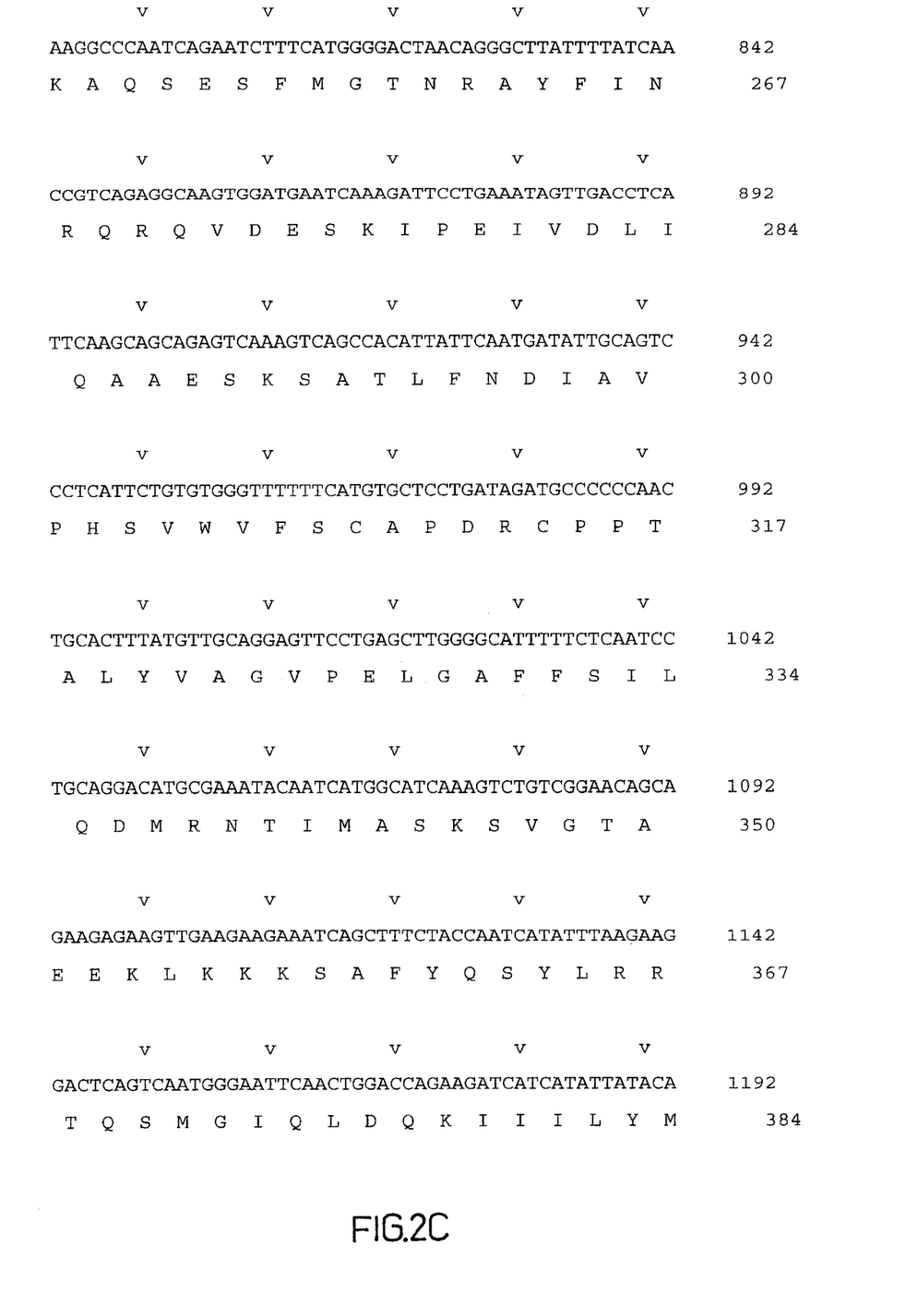
Figure 2D:
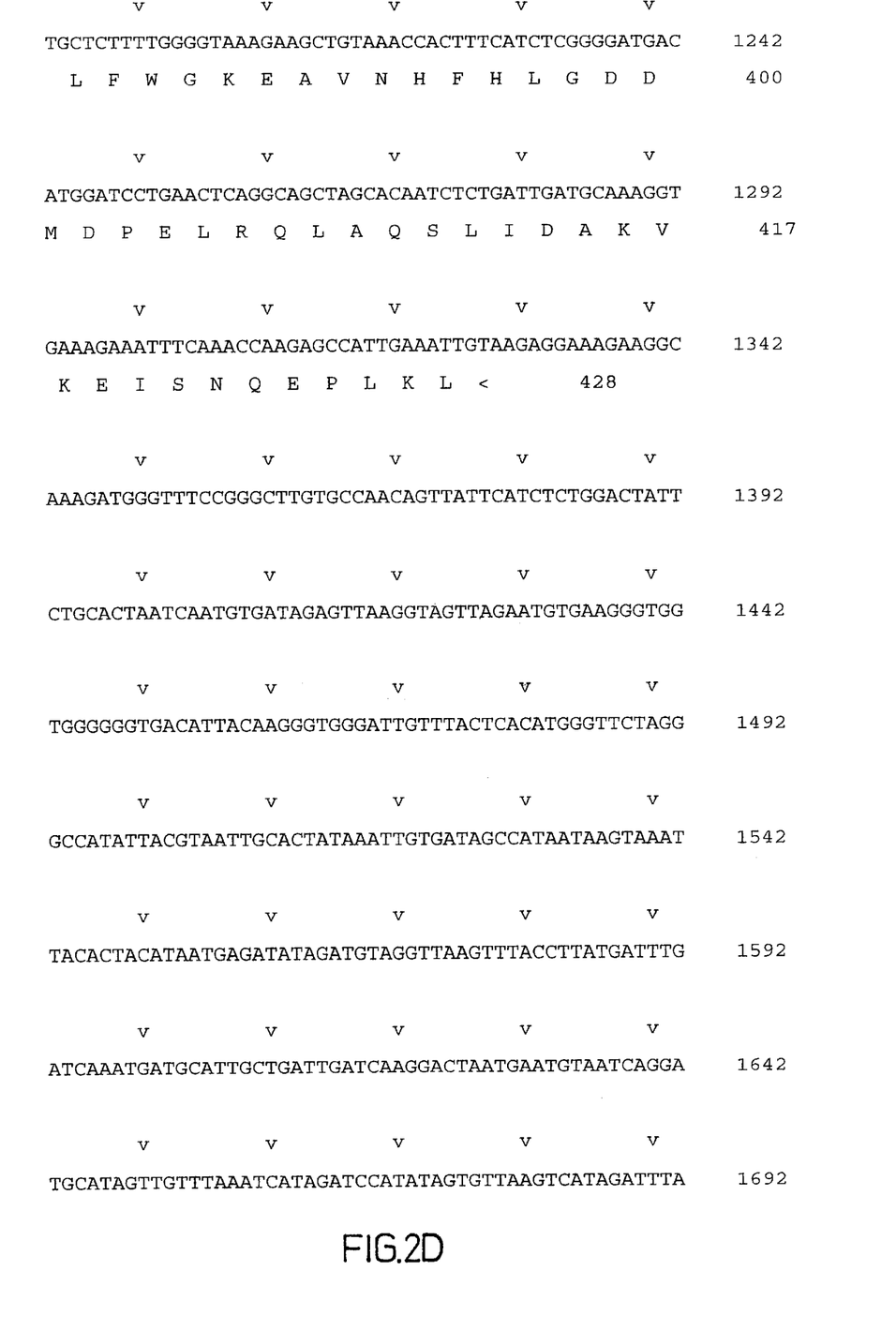
Figure 2E:
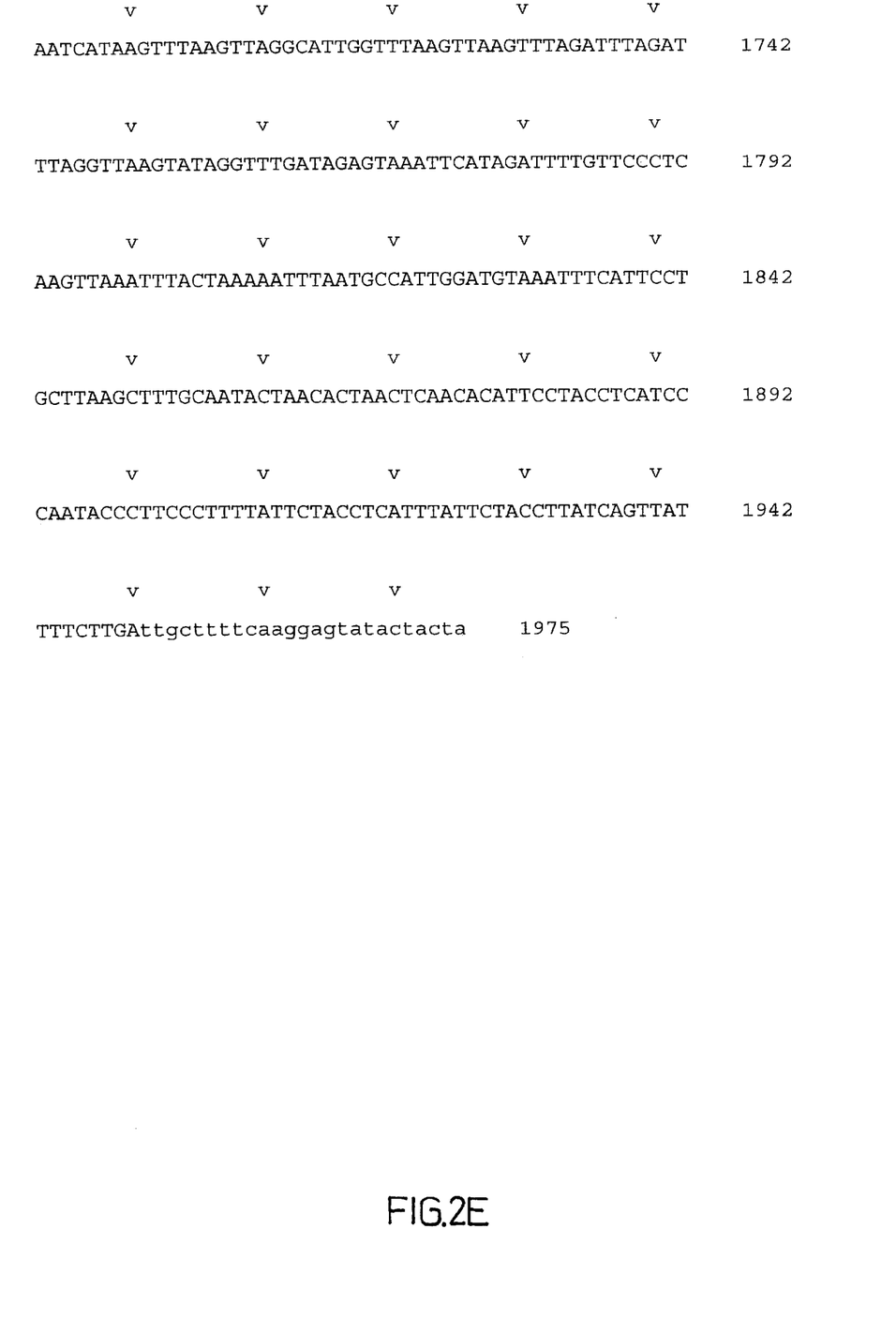
Figure 3:
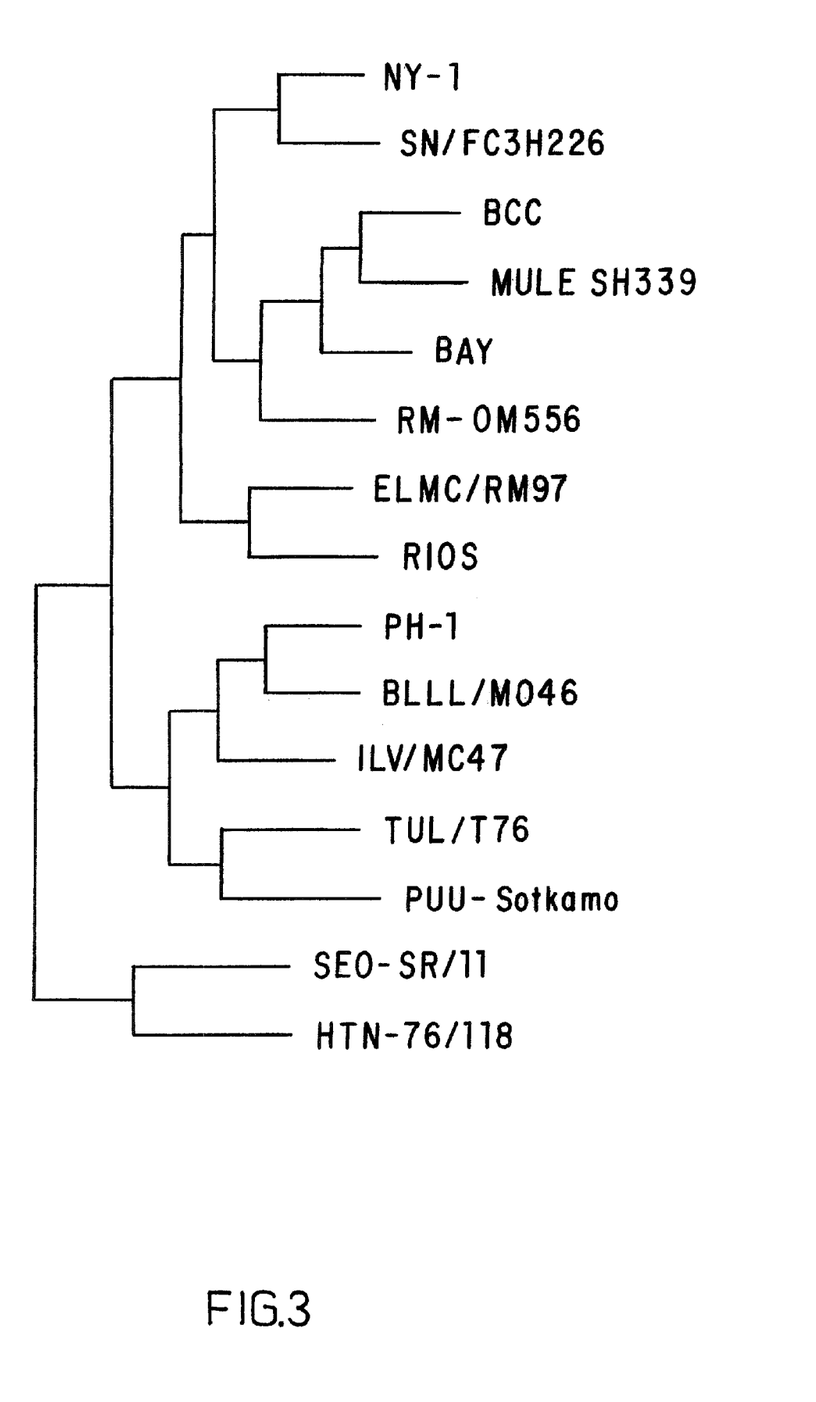
FIG. 3. Maximum-parsimony phylogenetic tree showing position of RMV (RM-OM556) relative to prototypical Hantaviruses BAY (Bayou), SNV (SN), Hantaan (HTN, Puumala (PUU), (Isla Vista (ILV), Tula (TUL), Bloodland Lake (BLLL), New York (N.Y.), El Moro Canyon (ELMC), Black Creek Canal (BCC), Rio Segundo (RIOS), Prospect Hill (PH) and Muleshoe (MULE). The tree is based upon the entire N gene sequences (1287-nt).

The use of the pET 23b expression system is designed to allow the ready purification of recombinant antigens for preparation of ELISAs and "slot-blot" format assays such as the RIBA™ (Chiron Corporation). These assays require that the antigen be extremely pure, because they are subject to false reactivities that can be associated with even small amounts of contaminating *E coli* antigens. The purification of the recombinant proteins is facilitated by the presence in the pET 23b of a genetic segment that encodes a "histidine tag", ie, a series of 6 histidine residues in tandem. This peptide tag has high affinity for certain metal ions (Cesium, Nickel) that can be incorporated into an affinity column. The Novagen Corporation sells such columns as kits for purification of recombinant proteins. These columns were purchased and found to work very well for purification of the RMV N protein. The purified N protein was placed on western blots and in microtiter wells, and probed with serum from animals and humans with and without Hantavirus infection (FIG. 1). Strong immunoreactivity of the RMV N protein was evident in these studies, indicating that it is useful in detection of Hantavirus antibodies.

III. Preparation of Recombinant Antigens. II. Use in Development of Antiviral Antibodies After expressing recombinant proteins in *E coli* or baculovirus systems from our rDNA RMV clones, the proteins are purified and used to immunize rabbit, mica and/or other animals by injection. The resultant antibodies (both polyclonal and monoclonal) are useful in diagnosis, treatment, or prophylaxis of RMV infection in the following ways. (1) As a method for amplification of any specific signal in an ELISA system (such as that described above) designed to detect antiviral antibodies in humans or animals; (2) as a reagent for detecting viral antigens, either in tissue samples or peripheral blood of humans or animals with possible RMV infection, or in cell cultures; (3) as potential sources of passive immunizations of humans with exposure to, or disease caused by, RMV. Passive antibodies are routinely used as prophylaxis after exposure to viruses such as rabies and hepatitis B virus.

IV. Preparation of Recombinant Antigens. III. Use in Development of Vaccines Molecular clones encoding a majority of the antigenic domains of RMV are potentially important vaccination reagents. While many possible approaches can be foreseen as a means of exploiting these reagents, the following are particularly contemplated. (1) The RMV N antigen is expressed in cultured cells under the control of a vaccinia or other heterologous virus' replication machinery, and used to prepare live or killed-virus vaccinia antigens. (2) The RMV DNA is used as a substrate for "naked DNA vaccines", i.e., immunization by injection of purified RMV DNA intramuscularly into humans or animals. (3) Purified RMV N protein, expressed in baculovirus, yeast, or *E. coli*, is injected into humans or animals in combination with a customary pharmacological carrier to allow development of an immune response and protective immunity.

V. Development of a PCR Diagnosis for RMV

Alternative reverse transcriptase-PCR-based systems for diagnosis of RMV in humans and animals may be used. While one system has been described herein, we expect that the following goals for improved diagnostic PCR may be met by using a system of this design. (1) A PCR system with increased sensitivity, made possible by choosing primer pairs designed solely from RMV sequences, as opposed to primers designed on the basis of conservation of sequences of related viruses. (2) A system with greater potential for decontamination, made possible by choosing a larger PCR target (such as 300 nt). Such a modification should make the system less prone to false positive tests. With the sequence of the entire RMV S genome in hand, many primer sets for the virus are possible.

PCR can be conducted quantitatively. It is expected that successful treatment of RMV infection will result in a rapid drop in the level of circulating virus during the course of a patient's treatment. We intend to explore that possibility, with the intent of developing a routine method for monitoring the efficacy of various therapies for HPS.

VI. Use of RMV Clones for in Situ Hybridization

The availability of the RMV S genome sequence allows the preparation of specific probes for detection of RMV RNA in cell culture, in human and animal tissues, and in human blood cells. Specific probes can be made to either strand of the virus. Plus strand probes, corresponding to the mRNA of the virus, should be useful in detecting RMV (a minus-strand virus), wherever it occurs. Minus strand probes should be useful in detecting the antigenomic strand and mRNA of RMV, which would occur only in tissues in which the virus is replicating. In situ hybridization has great potential as a research tool for understanding the replication of the virus, and some potential as a diagnostic, prognostic, or therapeutic tool if it proves able to detect replicating and non-replicating RMV in patient blood specimens, human or animal tissues, or viral cultures. This method is developed by expressing radio labeled RNA from DNA clones of the RMV in vitro, and using the RNA probes as reagents for in situ hybridization studies of infected tissues.

In the following claims, the claimed nucleotide or peptide sequences which are substantially equivalent in structure and function.

What is claimed is:

1. An isolated, purified, recombinant, and antigenic polypeptide of the Rio Mamore hantavirus (RMV) comprising SEQ. ID NO: 13 or an antigenic portion thereof that reacts specifically with RMV specific antibodies.

2. A method for the detection of hantavirus-specific antibodies in a sample comprising the following immunoassay steps:
   a) obtaining and preparing a tissue or serum sample suspected of containing hantavirus-specific antibodies;
   b) contacting the sample of step (a) with one or more of the antigenic polypeptides of claim 1 so as to permit formation of antigen-antibody complexes between at least one of said polypeptides and said hantavirus-specific antibodies; and
   c) detecting the presence or absence of said antigen-antibody complexes wherein the presence of said antigen-antibody complexes detects hantavirus specific antibodies in said sample.

3. The method of claim 2, wherein the immunoassay is an ELISA or western blot assay.

4. A recombinant peptide comprising the peptide sequence of SEQ ID NO:13 or an antigenic domain thereof.

* * * * *

SEQUENCE LISTING

<160> NUMBER OF SEQ ID NOS: 13

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 1
tagtagtaga ctccttgaga agctac                                    26

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 2
actactgcat atgctggtat gag                                       23

<210> SEQ ID NO 3
<211> LENGTH: 25

```
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 3
tctatgactt aacactatat ggatc                                        25

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 4
taagcttatg agcaacctcc aagaagtaca aga                               33

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 5
cctcgagcaa tttcaatggc tcttggtttg a                                 31

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 6
ctttatgttg caggwgtwcc tga                                          23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 7
atcctgcagg ayatgmgaaa tac                                          23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 8
cgggcagctg tgtctgcatt gga                                          23

<210> SEQ ID NO 9
<211> LENGTH: 23
<212> TYPE: DNA
```

-continued

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 9
ggtgtgattt catctgcytt cat                                         23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 10
cctacagact ttgatgccat dat                                         23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: PCR Primer
      to amplify RMV cDNA

<400> SEQUENCE: 11
tagtagtata ctccttgaaa agcaa                                       25

<210> SEQ ID NO 12
<211> LENGTH: 1975
<212> TYPE: DNA
<213> ORGANISM: Rio Mamore hantavirus

<400> SEQUENCE: 12
tagtagtaga ctccttgaga agctactact gcatatgctg gtatgagcaa cctccaagaa    60
gtacaagaag gtatcacact ccatgaacag cagcttgtag ctgctcgtca aaaacttaag   120
gatgccgaga aggcagtgga agtggaccca gatgacgtta caagagcac attacaaagc   180 agacgggcag ctgtgtctac attggagaat aaactcgcag aactcaagag acagctggca   240
gatttggtgg cagctcaaaa actggcttca aaaccagttg atccaacagg gcttgagcct   300
gatgaccatt taaaggagaa atcagctctg cgatatggga atgttctgga tgtgaactct   360
atagatcttg aagagcctag tggtcagact gcagattgga aagcaatcgg ggcatatatt   420
ttaggatttg tcataccgat tgtcctgaaa gccttataca tgctttcaac aagggggagg   480
caaactgtca agagaacaa agggacaaga ataaggttca aggatgactc atcttttgag   540
gaaataaatg ggattaggaa accgaaacat ctgtatgtct ccatgccaac agctcagtct   600
accatgaagg cagatgagat cacaccaggg aggtttcgaa caattgcctg tggtttattt   660
cctgcacaaa tcaaagctcg gaatatcatc agtccagtga tggggtgat tgggtttggg   720 ttctttgtaa aggactggat ggataggata gaaagttttt tagcagctga atgcccattc   780
ctcccaaaac caaaggccca atcagaatct ttcatgggga ctaacagggc ttattttatc   840
aaccgtcaga ggcaagtgga tgaatcaaag attcctgaaa tagttgacct cattcaagca   900
gcagagtcaa agtcagccac attattcaat gatattgcag tccctcattc tgtgtgggtt   960
ttttcatgtg ctcctgatag atgccccca actgcacttt atgttgcagg agttcctgag  1020
cttggggcat ttttctcaat cctgcaggac atgcgaaata caatcatggc atcaaagtct  1080
```

-continued

```
gtcggaacag cagaagagaa gttgaagaag aaatcagctt tctaccaatc atatttaaga    1140
aggactcagt caatgggaat tcaactggac cagaagatca tcatattata catgctcttt    1200
tggggtaaag aagctgtaaa ccactttcat ctcggggatg acatggatcc tgaactcagg    1260
cagctagcac aatctctgat tgatgcaaag gtgaaagaaa tttcaaacca agagccattg    1320
aaattgtaag aggaaagaag gcaaagatgg gtttccgggc ttgtgccaac agttattcat    1380
ctctggacta ttctgcacta atcaatgtga tagagttaag gtagttagaa tgtgaagggt    1440
ggtggggggt gacattacaa gggtgggatt gtttactcac atgggttcta gggccatatt    1500
acgtaattgc actataaatt gtgatagcca taataagtaa attacactac ataatgagat    1560
atagatgtag gttaagttta ccttatgatt tgatcaaatg atgcattgct gattgatcaa    1620
ggactaatga atgtaatcag gatgcatagt tgtttaaatc atagatccat atagtgttaa    1680
gtcatagatt taaatcataa gtttaagtta ggcattggtt taagttaagt ttagatttag    1740
atttaggtta agtataggtt tgatagagta aattcataga ttttgttccc tcaagttaaa    1800
tttactaaaa atttaatgcc attggatgta aatttcattc ctgcttaagc tttgcaatac    1860
taacactaac tcaacacatt cctacctcat cccaataccc ttccctttta ttctacctca    1920
tttattctac cttatcagtt attttcttga ttgcttttca aggagtatac tacta         1975
```

<210> SEQ ID NO 13
<211> LENGTH: 428
<212> TYPE: PRT
<213> ORGANISM: Rio Mamore hantavirus

<400> SEQUENCE: 13

```
Met Ser Asn Leu Gln Glu Val Gln Glu Gly Ile Thr Leu His Glu Gln
  1               5                  10                  15

Gln Leu Val Ala Ala Arg Gln Lys Leu Lys Asp Ala Glu Lys Ala Val
                 20                  25                  30

Glu Val Asp Pro Asp Asp Val Asn Lys Ser Thr Leu Gln Ser Arg Arg
             35                  40                  45

Ala Ala Val Ser Thr Leu Glu Asn Lys Leu Ala Glu Leu Lys Arg Gln
         50                  55                  60

Leu Ala Asp Leu Val Ala Ala Gln Lys Leu Ala Ser Lys Pro Val Asp
 65                  70                  75                  80

Pro Thr Gly Leu Glu Pro Asp Asp His Leu Lys Glu Lys Ser Ala Leu
                 85                  90                  95

Arg Tyr Gly Asn Val Leu Asp Val Asn Ser Ile Asp Leu Glu Glu Pro
            100                 105                 110

Ser Gly Gln Thr Ala Asp Trp Lys Ala Ile Gly Ala Tyr Ile Leu Gly
        115                 120                 125

Phe Val Ile Pro Ile Val Leu Lys Ala Leu Tyr Met Leu Ser Thr Arg
130                 135                 140

Gly Arg Gln Thr Val Lys Glu Asn Lys Gly Thr Arg Ile Arg Phe Lys
145                 150                 155                 160

Asp Asp Ser Ser Phe Glu Glu Ile Asn Gly Ile Arg Lys Pro Lys His
                165                 170                 175

Leu Tyr Val Ser Met Pro Thr Ala Gln Ser Thr Met Lys Ala Asp Glu
            180                 185                 190

Ile Thr Pro Gly Arg Phe Arg Thr Ile Ala Cys Gly Leu Phe Pro Ala
        195                 200                 205

Gln Ile Lys Ala Arg Asn Ile Ile Ser Pro Val Met Gly Val Ile Gly
    210                 215                 220
```

-continued

```
Phe Gly Phe Phe Val Lys Asp Trp Met Asp Arg Ile Glu Ser Phe Leu
225                 230                 235                 240

Ala Ala Glu Cys Pro Phe Leu Pro Lys Pro Lys Ala Gln Ser Glu Ser
                245                 250                 255

Phe Met Gly Thr Asn Arg Ala Tyr Phe Ile Asn Arg Gln Arg Gln Val
            260                 265                 270

Asp Glu Ser Lys Ile Pro Glu Ile Val Asp Leu Ile Gln Ala Ala Glu
        275                 280                 285

Ser Lys Ser Ala Thr Leu Phe Asn Asp Ile Ala Val Pro His Ser Val
    290                 295                 300

Trp Val Phe Ser Cys Ala Pro Asp Arg Cys Pro Pro Thr Ala Leu Tyr
305                 310                 315                 320

Val Ala Gly Val Pro Glu Leu Gly Ala Phe Phe Ser Ile Leu Gln Asp
                325                 330                 335

Met Arg Asn Thr Ile Met Ala Ser Lys Ser Val Gly Thr Ala Glu Glu
            340                 345                 350

Lys Leu Lys Lys Lys Ser Ala Phe Tyr Gln Ser Tyr Leu Arg Arg Thr
        355                 360                 365

Gln Ser Met Gly Ile Gln Leu Asp Gln Lys Ile Ile Ile Leu Tyr Met
    370                 375                 380

Leu Phe Trp Gly Lys Glu Ala Val Asn His Phe His Leu Gly Asp Asp
385                 390                 395                 400

Met Asp Pro Glu Leu Arg Gln Leu Ala Gln Ser Leu Ile Asp Ala Lys
                405                 410                 415

Val Lys Glu Ile Ser Asn Gln Glu Pro Leu Lys Leu
            420                 425
```